(12) United States Patent
Kim

(10) Patent No.: US 9,019,486 B2
(45) Date of Patent: Apr. 28, 2015

(54) MULTI-LIGHT FIBER SOURCE FOR FIBER END-SURFACE INSPECTION

(71) Applicant: Fluke Corporation, Everett, WA (US)

(72) Inventor: Wonoh Kim, Johns Creek, GA (US)

(73) Assignee: Fluke Corporation, Everett, WA (US)

( * ) Notice: Subject to any disclaimer, the term of this patent is extended or adjusted under 35 U.S.C. 154(b) by 0 days.

(21) Appl. No.: 13/755,265

(22) Filed: Jan. 31, 2013

(65) Prior Publication Data

US 2014/0211200 A1    Jul. 31, 2014

(51) Int. Cl.
*G01N 21/00* (2006.01)
*G01M 11/00* (2006.01)
*G01N 21/952* (2006.01)
*G01N 21/95* (2006.01)

(52) U.S. Cl.
CPC ............. *G01M 11/31* (2013.01); *G01N 21/952* (2013.01); *G01N 2021/9511* (2013.01)

(58) Field of Classification Search
CPC ............. G01N 21/952; G01M 11/31–11/319; G01M 11/37; G01M 11/33–11/338

USPC ........................................................ 356/73.1
See application file for complete search history.

(56) References Cited

U.S. PATENT DOCUMENTS

| | | | | |
|---|---|---|---|---|
| 4,583,851 | A | * | 4/1986 | Yataki ........................ 356/73.1 |
| 4,924,087 | A | * | 5/1990 | Bailey et al. ................ 356/73.1 |
| 5,140,167 | A | * | 8/1992 | Shaar et al. ............... 250/559.22 |
| 5,172,421 | A | * | 12/1992 | Nakamura et al. ............ 382/141 |
| 5,179,419 | A | * | 1/1993 | Palmquist et al. ........... 356/73.1 |
| 5,375,179 | A | * | 12/1994 | Shaar et al. .................... 385/15 |
| 5,448,365 | A | * | 9/1995 | Grollimund et al. .......... 356/430 |
| 6,597,455 | B1 | * | 7/2003 | Wlodarski et al. ............ 356/430 |
| 7,212,280 | B1 | * | 5/2007 | Fardeau ...................... 356/73.1 |
| 7,667,831 | B2 | * | 2/2010 | Koudelka et al. ............ 356/73.1 |
| 7,864,334 | B2 | * | 1/2011 | Jeong ............................ 356/496 |
| 8,072,593 | B2 | | 12/2011 | Brittain et al. |
| 2005/0134838 | A1 | * | 6/2005 | Hartmann et al. .......... 356/237.1 |
| 2010/0172614 | A1 | * | 7/2010 | Oota et al. ....................... 385/45 |

* cited by examiner

*Primary Examiner* — Michael A Lyons
*Assistant Examiner* — Shawn Decenzo
(74) *Attorney, Agent, or Firm* — Locke Lord LLP; Scott D. Wofsy; Christopher J. Capelli

(57) ABSTRACT

A fiber end-surface inspection device and method illuminates the fiber end-surface from at least 2 different illumination angles, taking observations at the different angles, for detection of fiber end-surface imperfections, scratches or the like.

9 Claims, 5 Drawing Sheets

MULTI-LIGHT FIBER SOURCE FOR FIBER END-SURFACE INSPECTION

BACKGROUND

This disclosure relates to testing of fiber optic communication lines, and more particularly to the inspection of the end surfaces of fiber optic cables.

Current fiber inspection probes (or cameras) in the market use one fixed light (for example, a LED or light bulb) that shines light through a prism onto the fiber end-surface for inspection. The detection of defects on fiber end-surface can be dependent on the angle of the single light source provided with a typical fiber inspection tool. With a typical single light source tool, in a particular case it may be that a scratch cannot be detected from first inspection, but, upon a user manually rotating or otherwise maneuvering the fiber to get different angles of light falling on the fiber end, scratches that might not be visible at first, may come into view.

To inspect dirt or chirp of fiber connector-end, a small fiber scope (or probe) is typically used. In machine vision systems, light source is one of the key factors. Some of the big scope stations use fiber ring light sources and other small scopes use a LED light next to the scope. If the light shades from center or perimeter like fiber ring light source, some of the defects (dirt, chirp, or scratch) are difficult to find because defects can be obscured by shadows. On the other hand, if the light is from side, the other half of the fiber-end becomes dark because the fiber-end is not a straight plane but instead has curvature. Thus, some experienced technicians rotate the fiber to inspect the other side of the fiber end. However, this method does not work with angled connectors and with automated fiber-end inspection system using machine vision. Also, requiring such manual movement to accomplish testing adds a factor of operator skill to the reliability of the test results, which is undesirable.

SUMMARY

In accordance with the disclosure, a fiber end-surface inspection tool provides dual (or multiple) light sources for inspection, and can toggle the application of light from the different sources, providing improved scratch detection.

Accordingly, it is an advantage of the present disclosure to provide an improved fiber end-surface inspection tool.

It is a further advantage of the present disclosure to provide an improved method for inspecting fiber optic communication line fiber end-surfaces.

It is yet another advantage of the present disclosure to provide an improved system for inspecting the end-surfaces of fiber optic cables.

The subject matter of the present technology is particularly pointed out and distinctly claimed in the concluding portion of this specification. However, both the organization and method of operation, together with further advantages and embodiments thereof, may best be understood by reference to the following description taken in connection with accompanying drawings wherein like reference characters refer to like elements.

DETAILED DESCRIPTION

The system according to a preferred embodiment of the present disclosure comprises a device that uses two (or more) LEDs positioned at locations to provide different angles of application of the light source. In operation, first, one LED is turned on, and an image of the fiber end-surface is taken. Then, that first LED is turned off and the second LED is turned on, and another image is taken, providing multiple angles of applied light automatically, without requiring the operator to manually rotate, or maneuver the fiber or the light source.

Figure 1:
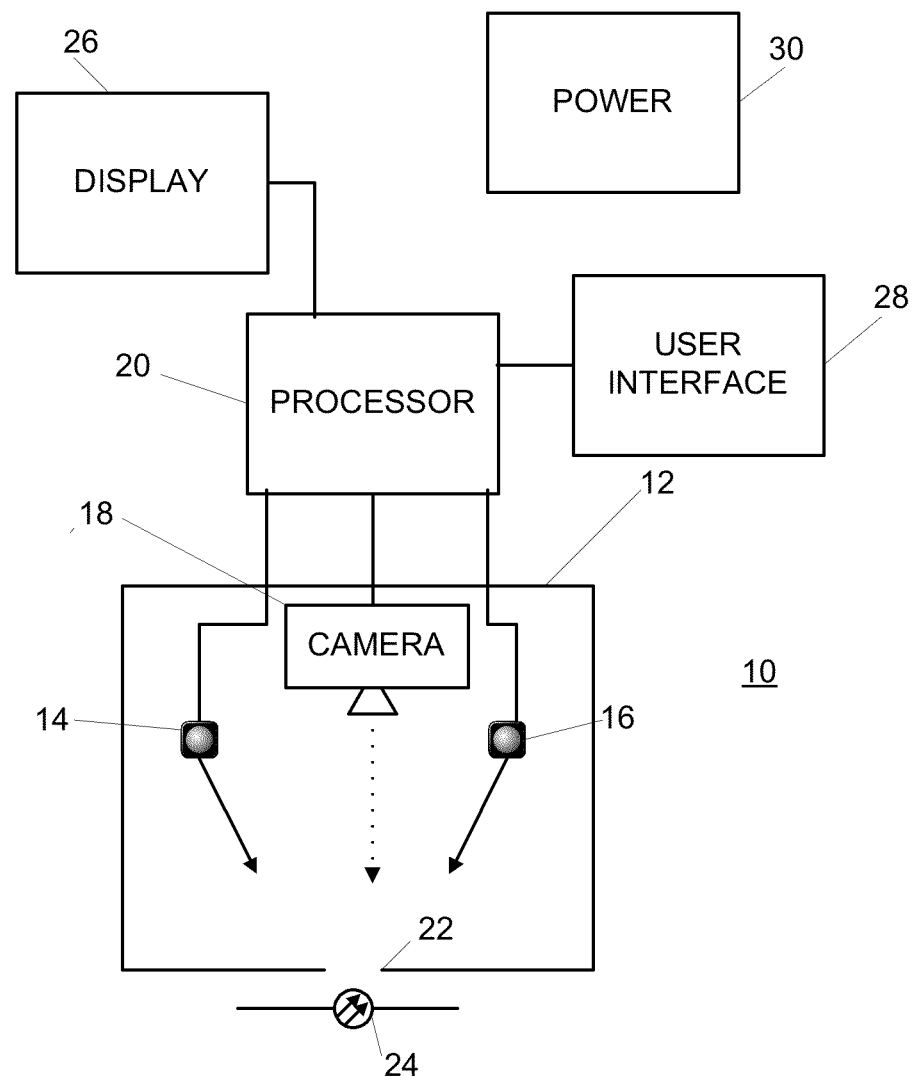
FIG. 1 is a block diagram of a device in accordance with the present disclosure.

Referring to FIG. 1 a block diagram of a test device 10 in accordance with the disclosure, the device includes a test chamber 12 (which may comprise an open air space), having first and second light sources 14, 16, suitably LEDs in a particular embodiment, with the 2 LEDs positioned at alternated sides of a camera 18. The camera and LEDs are controlled by/communicate with a processor 20. Camera 18 observes viewing position 22 which is positioned at or receives therein a fiber optic cable end 24 therein, for inspection.

A display 26 for displaying results, images and providing a control interface (in conjunction with user interface 28 (e.g., keys or touch screen functionality) also interfaces with the processor. Power supply 30, which can be battery or AC mains supply, provides power to operate the device.

Figure 2:
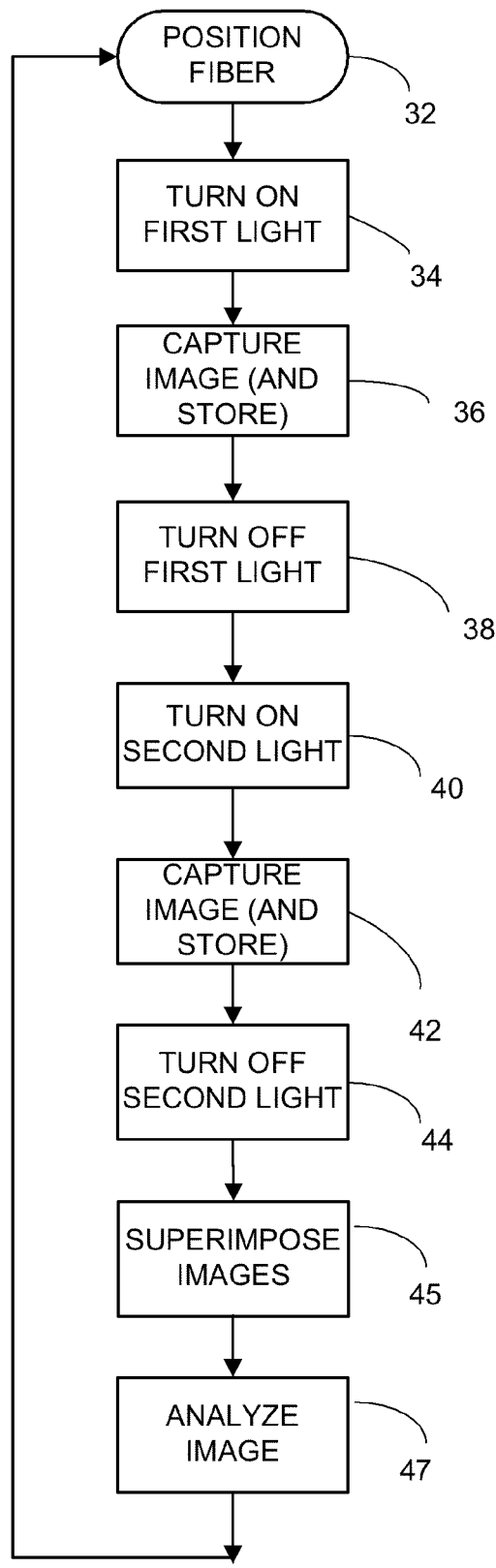
FIG. 2 is a flow chart of the operational steps of performing tests with the device of FIG. 1.

Referring now to FIG. 2, a flow chart of the operational steps of testing a fiber end-surface, first, the fiber is positioned (step 32) at an inspection site (for example, viewing position 22), whereupon the first light (assuming a 2 light system) is turned on (step 34) and an image of the fiber end-surface is captured (step 36), and provided to the processor or otherwise stored. Next, the first light is turned off (step 38) and the second light is turned on (step 40), providing illumination of the fiber surface from a different light angle. An image is captured (step 42) and stored or otherwise held for further use, and the second light is turned off (step 44). The resulting images may be superimposed (step 45), employing the images taken in different directions to get a complete image that contains defects observed in every directions. The resulting combined image, that contains all the defects as observed from the multiple angles of illumination, may be processed (step 47) by image processing algorithm to detect defects automatically.

The resulting images may be displayed also for visual inspection by an operator of the device, thereby providing detection of defects, scratches, etc.

The operation may be automated by processor 20, in conjunction with the camera to automatically detect when a fiber is present, or can be performed under direction of a user.

Figure 3:
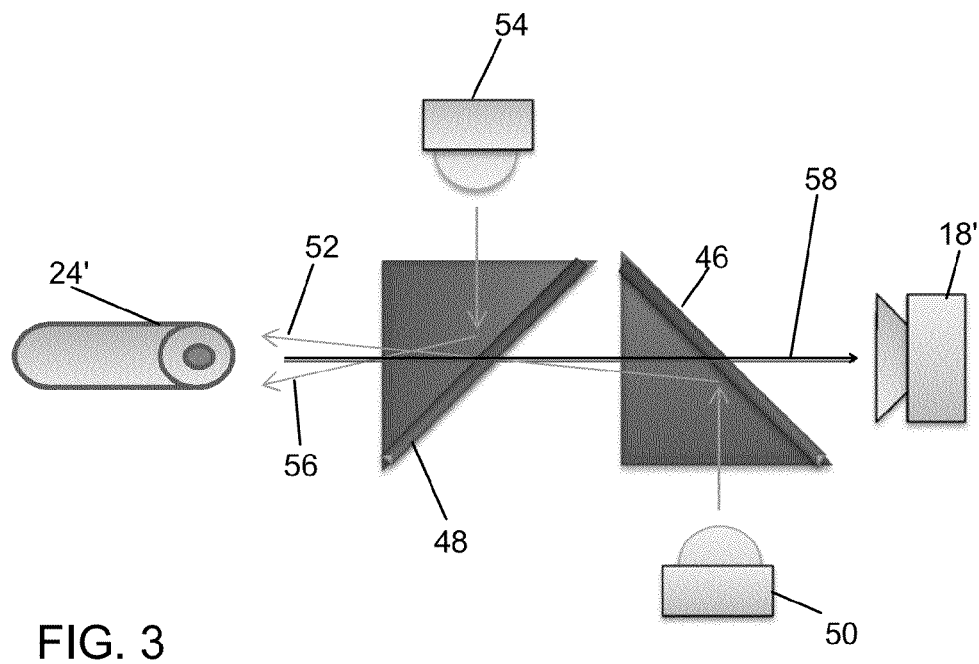
FIG. 3 is a view of an implementation of the light sources and camera.

FIG. 3 is an illustration of a two light source illumination system wherein camera 18' observes the fiber under test 24' through first and second coated prisms which are positioned in line with one another, with their reflection direction oriented towards the fiber under test. First prism 46 is closest to camera 18', and receives and reflects light from light source 50 at orientation 52. Second prism 48 is spaced between the first prism and the fiber under test, with its reflective surface directed to reflect towards the fiber under test. Light source 54 is positioned to provide light to the prism 48, which is reflected towards the fiber under test at orientation 56. The prisms are positioned such that orientations 52 and 56 provide light to the fiber under test at different angles. As is known in the art, the prisms reflect part (typically half) of light from the light sources, and part of the light reflected from the surface of the fiber under test is transmitted to camera 18' which observes the reflected light 58 from the fiber under test as passed through the prisms. The illumination of lights sources 50, 54 may be accomplished in accordance with the steps of FIG. 2, wherein the light sources are alternately illuminated.

Figure 4:
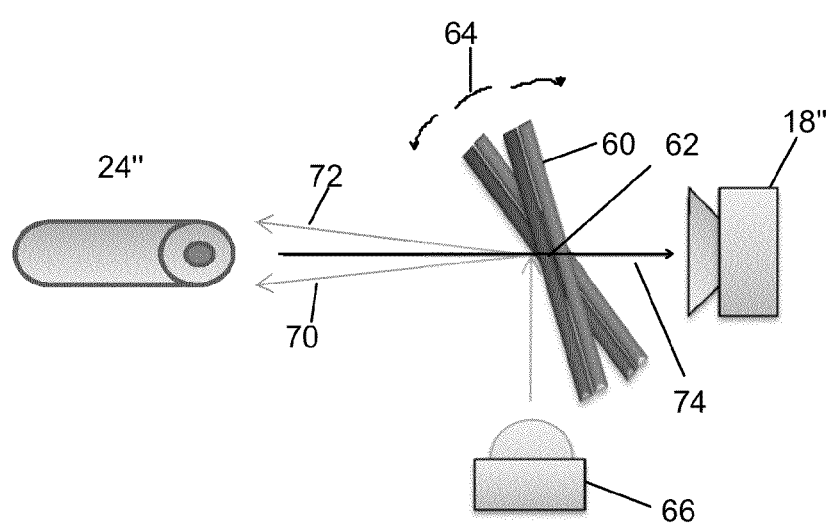
FIG. 4 is a view of an alternative implementation of the light source and camera, using a variable angle mirror.

FIG. 4 illustrates an alternate embodiment employing a single light source and an alternating angled mirror to provide different angles of light injection to the fiber under test. Partial mirror 60 is positioned between camera 18' and fiber under test 24', with the mirror adapted to be pivoted about axis 62 as illustrated by arc 64. Two possible positions of the mirror are illustrated in FIG. 4, a left-most and right-most position (when considered from the top of the mirror in FIG. 4) Light source 66 shines light 68 to the reflective surface of the mirror, causing reflected light 70, 72 to be transmitted to the fiber under test, reflected light 72 coming from the mirror when in the right-most tilt position and reflected light 70 coming from the mirror when in the left-most tilt position. Camera 18' then observes the reflected light from the fiber under test.

Figure 5:
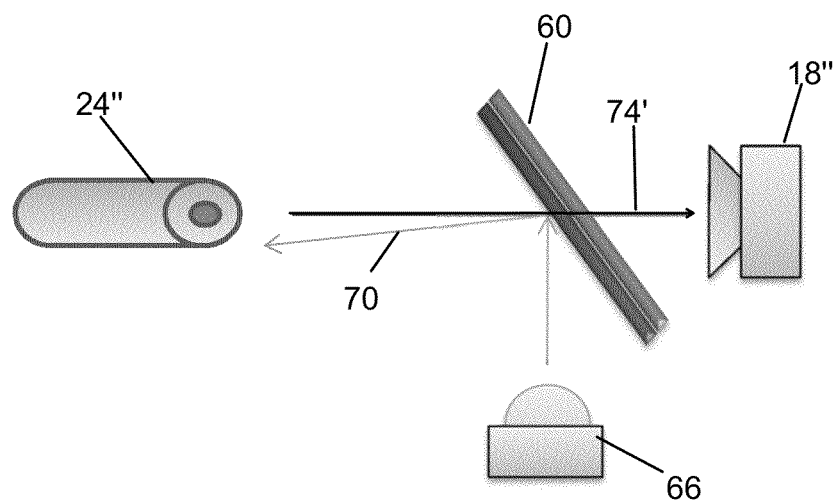
FIG. 5 is a view of the system of FIG. 4 with the mirror at a first angle.
Figure 6:
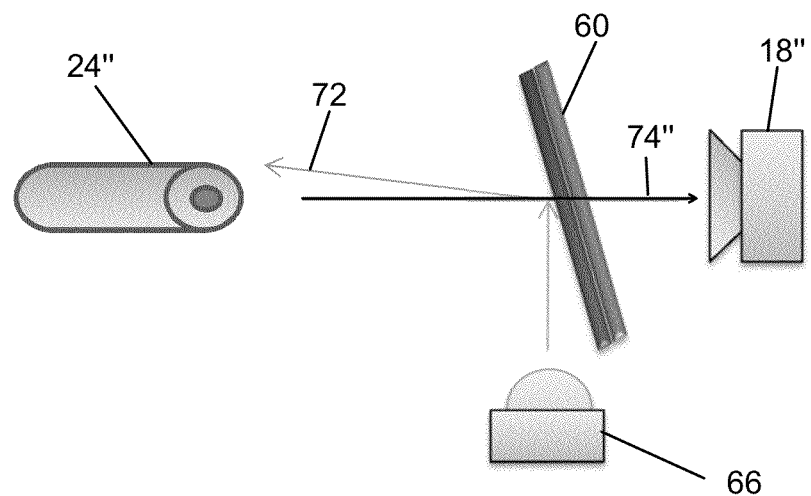
FIG. 6 is a view of the system of FIG. 4 with the mirror at a second angle.

FIG. 5 is representative of the setup with the mirror in a first, left-most position, and illustrates the transmission 70 and reflection 74' of light with the mirror at a first angle, while FIG. 6 illustrates the transmission, and reflection of light with the mirror at a second angle. The fiber under test is thus illuminated with light from two different angles. Configurations may be employed that alter the mirror angle to more than 2 different angles.

Figure 7:
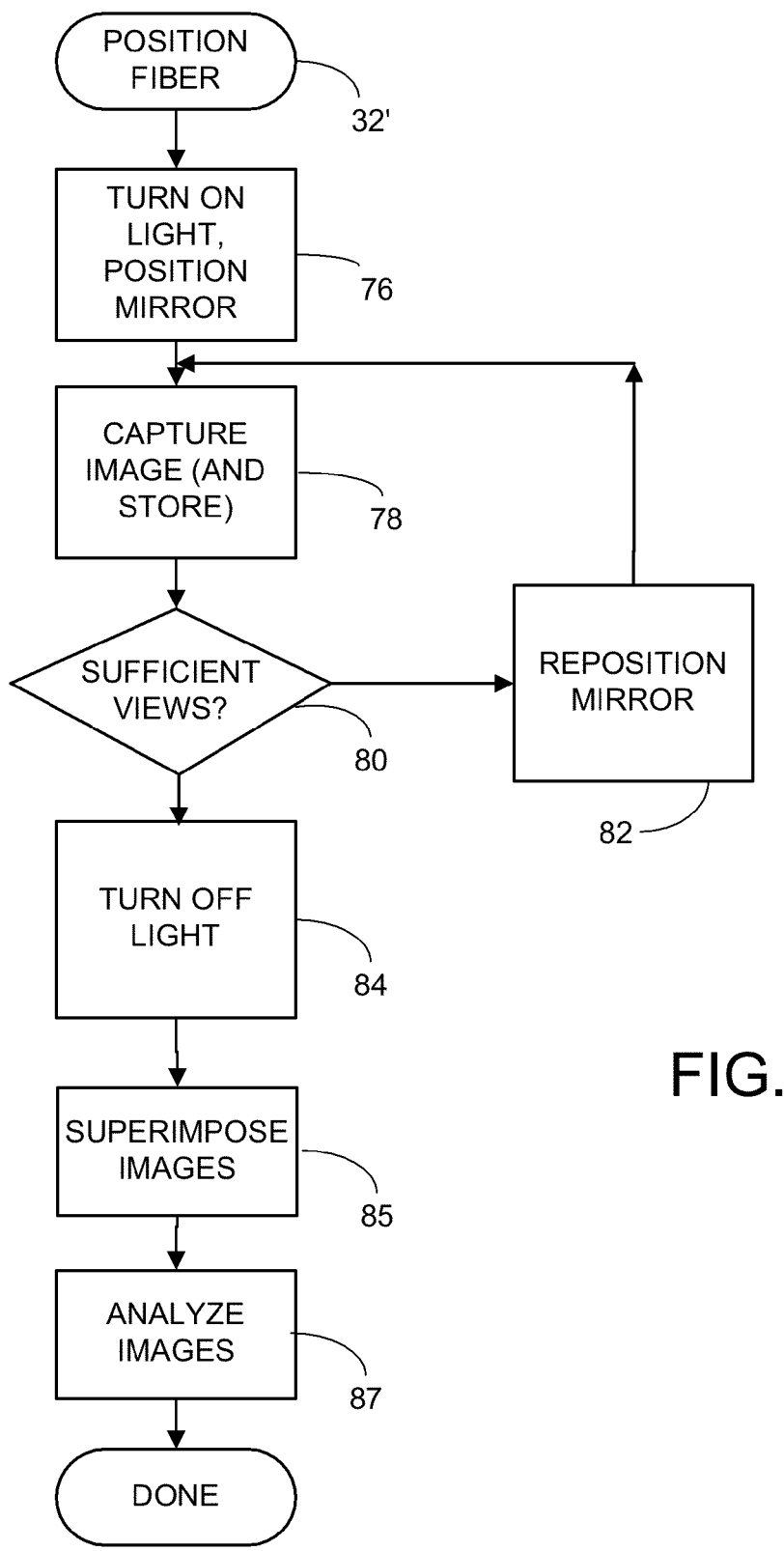
FIG. 7 is a flowchart of the operational steps with a pivoting mirror configuration.

FIG. 7 is a flowchart of the operational steps with a pivoting mirror configuration, wherein the fiber is positioned for inspection at step 32', the light source 66 is illuminated and the mirror 60 is moved to a first position, step 76. An image is then captured at step 78 and suitably stored for future use and processing. Next, a decision is made as to whether sufficient images have been captured. Ideally 2 or more different mirror position images would be taken. If a sufficient number have not been taken, then in block 82 is entered to reposition the mirror to a different angle then previously employed, and the process loops back to block 78 to capture another image. If a sufficient or desired number of images have been captured at block 80, then the light source is turned off at step 84, the images taken and stored may be superimposed (step 85) to provide a single image having all the defects as detected from various angles of illumination, and analysis may be performed on the combined image (step 87) and the process is complete.

An alternative embodiment employs multiple light sources, for example more than 2 total, with the light sources positioned spatially in different locations to provide additional angles of light illumination of the fiber under test, or, as noted above, by angling of mirror 60 to more than 2 different angles relative to the fiber under test.

Still further, a single light source may be employed, with direction of the light through a splitter or other method so as to provide illumination of the fiber end-surface from more than one angle.

The test device may be implemented as a hand held/portable device, or a bench top test unit, for example.

Accordingly, an improved method and device for inspecting fiber end-surfaces is provided.

While a preferred embodiment of the technology has been shown and described, it will be apparent to those skilled in the art that many changes and modifications may be made without departing from the broader aspects. The appended claims are therefore intended to cover all such changes and modifications as fall within the true spirit and scope of the technology.

What is claimed is:

1. A fiber end-surface detection device, comprising:
   a first light source positioned to illuminate a first prism adapted to reflect light from the first light source toward the fiber end surface at a first illumination angle;
   a second light source positioned to illuminate a second prism adapted to reflect light from the second light source toward the fiber end surface at a second illumination angle, the second prism positioned between the first prism and the fiber end surface;
   a vision device for observing a reflection of the fiber end-surface under illumination from the first light source at the first illumination angle and under illumination from the second light source at the second illumination angle, wherein the reflection passes through the first and second prisms toward the vision device; and
   a controller for alternately illuminating said first light source and said second light source, for operating said vision device to take images of the fiber end-surface under said alternate illuminations and for operating said vision device to superimpose said images of the fiber end-surface taken under said alternate illuminations,
   wherein said first and second light sources are located on opposite sides with respect to the vision device position and wherein said fiber end-surface is rounded.

2. The fiber end-surface detection device according to claim 1, wherein said first and second light sources comprise LEDs.

3. The fiber end-surface detection device according to claim 1, further comprising plural additional light sources for illumination of the fiber-end surface from plural additional angles different from the first and second illumination angles and different from one another.

4. A method for inspection the end-surface of an optical fiber, comprising:
   providing a first light source, a second light source, a first prism and a second prism, so that said first and second light sources are located on opposite sides with respect to a vision device position and so that the first prism reflects light from the first light source toward the fiber end surface at a first illumination angle, the second prism reflects light from the second light source toward the fiber end surface at a second illumination angle, the second prism positioned between the first prism and the fiber end surface, a reflection of the fiber end surface passes through the first and second prisms towards the vision device;
   alternately illuminating said first light source and said second light source, wherein said first light source and said second light source are operated by a controller;
   taking images of the fiber end-surface under said alternate illuminations, wherein said images are taken by the vision device operated by the controller;
   superimposing said images of the fiber end-surface taken under said alternate illuminations to provide a combined image of multiple taken images, wherein said images are superimposed by the vision device operated by the controller; and observing said combined image of the fiber end-surface taken under said alternate illuminations, wherein said fiber end-surface is rounded.

5. The method according to claim 4, wherein said first and second light sources comprise LEDs.

6. The method according to claim 5, wherein said first and second illuminations angles are located on opposite sides with respect to the vision device position.

7. The method according to claim 6, further comprising providing plural additional light sources for illumination of the fiber-end surface from plural additional angles different from the first and second illumination angles and different from one another.

8. A fiber end-surface detection device, comprising:
a processor;
a first light source for illuminating a first prism adapted to reflect light from the first light source toward the fiber end surface at a first illumination angle;
a second light source for illuminating a second prism adapted to reflect light from the second light source toward the fiber end surface at a second illumination angle, the second prism positioned between the first prism and the fiber end surface; and
a vision device for observing a reflection of the fiber end-surface under illumination from the first light source at the first illumination angle and under illumination from the second light source at the second illumination angle, wherein the reflection passes through the first and second prisms toward the vision device,
wherein said first and second light sources are located on opposite sides with respect to the vision device position and wherein said processor alternately illuminates said first light source and obtains a first image of the fiber end-surface from said vision device, and illuminates said second light source and obtains a second image of the fiber end-surface and wherein said processor superimposes said first and second images of the fiber end-surface taken under said alternate illuminations to provide a combined image of the fiber end-surface, wherein said fiber end-surface is rounded.

9. The fiber end-surface detection device according to claim 8, wherein said first light source comprises a first LED, and said second source comprises a second LED and wherein said first and second illuminations angles are located on opposite sides with respect to the vision device position.

* * * * *